United States Patent
Kim et al.

[11] Patent Number: 6,034,087
[45] Date of Patent: Mar. 7, 2000

[54] NUCLEOSIDE DERIVATIVES AND PROCESS FOR PREPARING THEREOF

[75] Inventors: Jung Woo Kim; Chong Ryul Lee, both of Seoul; Koo Hun Chung, Kyeonggi-do; Soon Kil Ahn, Seoul; Kyung Hoi Cha; Hoe Joo Son, both of Kyeonggi-do; Sung Jo Choi, Seoul; Byeong Seon Jeong, Seoul; Kyeong Bok Min, Seoul, all of Rep. of Korea

[73] Assignee: Chong Kun Dang Corp., Seoul, Rep. of Korea

[21] Appl. No.: 08/817,611

[22] PCT Filed: Oct. 21, 1995

[86] PCT No.: PCT/KR95/00135

§ 371 Date: Jun. 11, 1997

§ 102(e) Date: Jun. 11, 1997

[87] PCT Pub. No.: WO96/12716

PCT Pub. Date: May 2, 1996

[30] Foreign Application Priority Data

Oct. 22, 1994 [KR] Rep. of Korea ............ 94-27067
Oct. 22, 1994 [KR] Rep. of Korea ............ 94-27068
Feb. 7, 1995 [KR] Rep. of Korea ............ 95-2124

[51] Int. Cl.[7] .................. A61K 31/52; C07D 473/18; C07D 473/40; C07D 473/30

[52] U.S. Cl. .................. 514/262; 514/266; 514/274; 544/243; 544/244; 544/264; 544/265; 544/276; 544/277; 544/309; 544/313; 544/317; 549/13; 549/21; 549/274; 549/378; 556/437

[58] Field of Search .................. 544/243, 244, 544/264, 265, 272, 267, 276, 277, 309, 316, 312, 313, 318, 315, 317; 514/262, 266, 274

[56] References Cited

U.S. PATENT DOCUMENTS

5,736,549 4/1998 Beasley .................. 544/277

FOREIGN PATENT DOCUMENTS

0 494 119 S1 7/1992 European Pat. Off.
0 515 144 A1 11/1992 European Pat. Off.
WO 92/10496 6/1992 WIPO.
WO 94/29301 12/1994 WIPO.
WO 95/29174 11/1995 WIPO.

OTHER PUBLICATIONS

Jung, Tet Letters 32(14)5717 1991.
Prisbe, J. Med. Chem 29, 2445 1986.
Vuilhorgne, Heterocycles 11, 495 1978.
Van Aerchot, Nucleoside Nucleotides 10, 591–2 1991.
Antiviral Activity of 2',3'—dideoxy–β–L–5–fluorocytidine (β–L–FddC) and 2',3'–dideoxy–β–L–cytidine (β–L–ddC) Against Hepatitis B Virus and Human Immunodeficiency Virus Type 1 in Vitro, Tai–Shun Lin et al., Biochemcial Pharmacology, vol. 47, No. 2, pp. 171–174, 1994.
Inhibition of the replication of hepatitis β virus in vitro by 2',3'–dideoxy–3'–thiacytidine and related analogues, Shin–Lian Doong et al., Proc. Natl. Acad. Sci. USA, vol. 88, pp. 8495–8499, Oct. 1991.

*Primary Examiner*—Mark L. Berch
*Attorney, Agent, or Firm*—Finnegan, Henderson, Farabow, Garrett & Dunner, L.L.P.

[57] ABSTRACT

Nucleoside derivatives represented by formula (I);

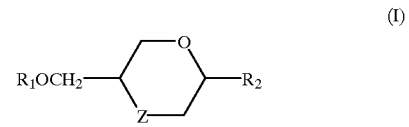

wherein, $R_1$ represents hydrogen, phosphate or phosphonate group, $R_2$ represents substituted or unsubstituted pyrimidine or purine base, and Z represents S, SO, $SO_2$, O or C; or pharmaceutically acceptable salts thereof. Compound (I) can be obtained by reacting a compound of the formula (II);

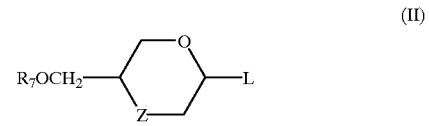

wherein, $R_7$ represents hydrogen or hydroxy-protecting group, L represents aromatic or nonaromatic acyl, halide or alkoxy, and Z represents S, SO, $SO_2$, O or C, with a base.

8 Claims, No Drawings

NUCLEOSIDE DERIVATIVES AND PROCESS FOR PREPARING THEREOF

This application is a 371 of PCT/KR95/00135, filed Oct. 21, 1995.

TECHNICAL FIELD

The present invention relates to novel nucleoside derivatives represented by following general formula (I);

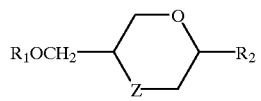
(I)

wherein, $R_1$ is hydrogen, phosphate or phosphonate group, $R_2$ is substituted or unsubstituted pyrimidine or purine base, and Z is S, SO, $SO_2$, O or C; showing excellent anti-HBV effect, and the process for preparing thereof.

Each compound represented by the general formula (I) has at least two chiral centers, and thus the optical isomers or mixtures thereof are also included in the present invention.

BACKGROUND ART

Hepatitis B Virus(HBV) is a lethal virus which causes acute/chronic Hepatitis in human body, and finally developes the disease into liver cancer. At present, a remedy for treating the viral disease does not exist though vaccines against the virus have been developed. Up to the present, Ara-A, interferon or the like has been used in treatment of Hepatitis B, however, there are many problems in view of effectiveness and safety.

Recently, various nucleoside compounds having anti-HBV activity have been reported. For example, 2',3'-dideoxy-3'-thiacytidine[Proc. Natl. Acad. Sci. USA, 88, 8495 (1991)], 5-fluoro-2',3'-dideoxy-3'-thiacytidine[Proc. Natl. Acad. Sci. USA, 88, 8495(1991)], 2'3'-dideoxy-β-L-5-fluoro-cytidine[Biochem. Pharm., 47, 171(1994)), 2',3'-dideoxy-β-L-cytidine[Biochem. Pharm., 47, 171(1994)], etc. are reported as showing anti-HBV activity.

However, these compounds reported up to the present have substantial need to be improved in view of effectiveness and safety. Therefore, it is required to develop novel compounds having excellent effectiveness with low toxicity.

DISCLOSURE OF INVENTION

The object of the present invention is to provide such novel compounds represented by the above general formula (I) showing excellent anti-HBV activity with low toxicity, and processes for preparing thereof.

The compounds of the present invention represented by general formula (I) are compounds of which $R_1$ is hydrogen, phosphate or phosphonate group, $R_2$ is pyrimidine or purine base of natural origin or slightly modified pyrimidine or purine base of natural origin, and Z is S, SO, $SO_2$, O or C.

More desirable compounds among the compounds of general formula (I) are those of which $R_1$ is hydrogen, phosphate or phosphonate, $R_2$ is selected from the groups represented by following formula, and Z is S, O or C.

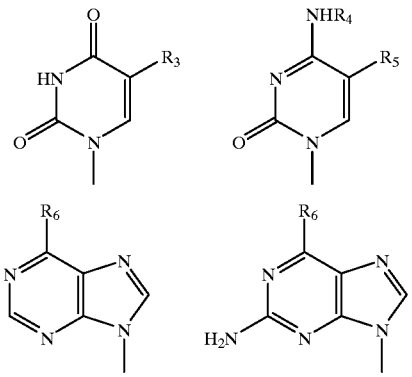

In the formula, $R_3$ is hydrogen, methyl, fluoro, chloro, bromo, iodo, trifluoromethyl, methoxymethyl or 2-bromovinyl group, $R_4$ is hydrogen or acyl group, $R_5$ is hydrogen, fluoro or methyl group, and $R_6$ is hydroxy, chloro or amino group.

The compound represented by formula (I) of the present invention can be obtained by reacting the compound represented by following formula (II);

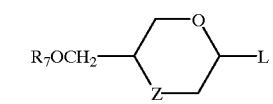
(II)

wherein, $R_7$ is hydrogen or hydroxyl-protecting group, preferably alkyl, acyl or substituted silyl group, more preferably benzyl, acetyl, benzoyl, trimethylsilyl, tert-butyldimethylsilyl or tert-butyldiphenylsilyl group, L is aromatic or nonaromatic acyl, halo or alkoxy group, preferably acetyl group, and Z is S, SO, $SO_2$, O or C, with appropriate base.

More specifically, the compound (I) is obtained by condensating the compound (II) with a base protected by silyl group in the presence of Lewis acid catalyst. Desirable solvents used in the reaction include methylene chloride, 1,2-dichloroethane and aceonitrile. Desirable Lewis acid catalyst includes tin chloride and trimethylsilyl triflate.

The 1,4-oxathiane compounds, kinds of compounds represented by general formula (II) used as starting material for the preparation of the compounds of general formula (I) also are novel compounds, and can be prepared according to the following reaction scheme.

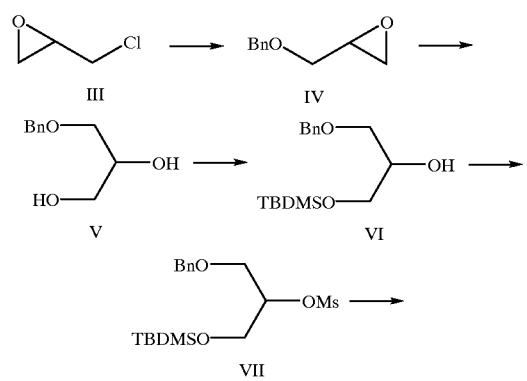

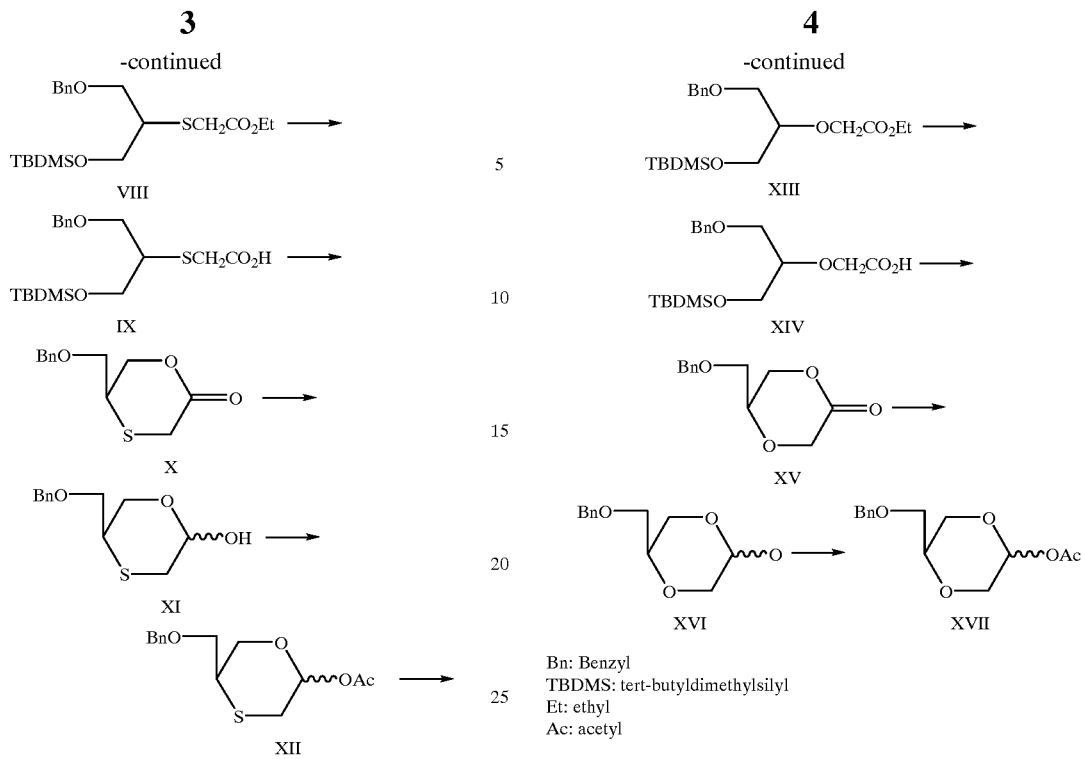

Bn: benzyl
Et: ethyl
Ms: mesyl
TBDMS: tert-butyldimethylsilyl
Ac: acetyl

According to a preferred embodiment of the present invention, compound (XII), a kind of compound (II), can be prepared as follows:

Epichlorohydrin (III) is reacted with, alcohol in the presence of base to provide epoxy compound (IV), which is hydrolysed with acid to obtain glycerol compound (V) of which one of the primary alcohol groups is protected. Another primary alcohol group is protected by substituted silyl group to provide glycerol compound (VI), and then the secondary alcohol group is mesylated to obtain compound (VII). The compound (VII) is reacted with ethyl 2-mercaptoacetate in the presence of base by substitution to obtain compound (VIII).

The obtained compound (VIII) was hydrolysed to provide hydroxyacid (IX), which is lactonized in the presence of acid catalyst to obtain compound (X). The compound (X) is reduced to provide lactol (XI), which is acetylated to obtain the desired compound (XII).

1,4-Dioxane compounds, kinds of compounds of general formula (II), used as starting material for preparing the compounds of general formula (I) are novel compounds, too, and can be prepared according to the following scheme.

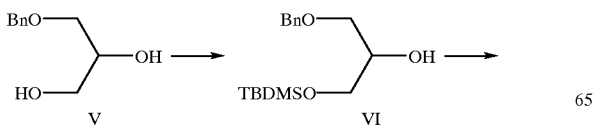

According to preferable embodiment of the present invention, compound (XVII), a kind of compound of general formula (II) can be prepared as follows;

The glycerol compound (V) of which one of the primary alcohol group is protected by benzyl was protected by substituted silyl group to provide compound (VI), which is reacted with ethylbromoacetate in the presence of base to obtain compound (XIII). The compound (XIII) is hydrolysed to provide hydroxyacid (XIV), which is lactonized in the presence of acid catalyst to obtain compound (XV). The lactone (XV) is reduced to provide lactol (XVI), which is acetylated to obtain compound(XVII).

Tetrahydropyrane compounds, kinds of compounds of general formula (II), used as starting material for preparing the compounds of general formula (I) are novel compounds, too, and can be prepared according to the following scheme.

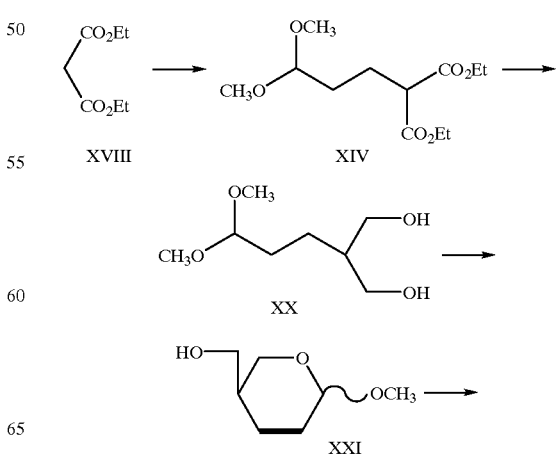

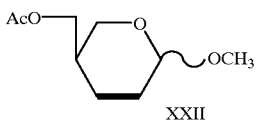

XXII

According to the reaction scheme above, diethylmalonate (XVIII) is reacted with bromopropionaldehyde dimethyl acetal to provide the alkylated compound (XIV), of which the ester group is reduced to obtain diol (XX). The compound (XX) is reduced in the presence of acid catalyst to provide tetrahydropyran compound (XXI), of which the hydroxy group is protected to obtain the desired product (XXII).

From the above reactions, the desired compound (I) is obtained as a mixture of cis and trans isomers, which can be separated by physical methods such as silica gel column chromatography or fractional crystallization.

Optically pure compounds of formula (I) can be also obtained by optical resolution of the racemic mixture or asymmetric synthesis starting from optically pure material.

Pharmaceutically acceptable salts can be obtained by dissolving the resultant compounds obtained above in an appropriate solvent, and then treating the solution with acid or base.

BEST MODE FOR CARRYING OUT THE INVENTION

Now, the present invention is further described by referring to the following examples. However, the present invention should not be understood to be limited to the examples.

EXAMPLE 1

Preparation of glycidyl benzyl ether (IV)

[Method A]

A solution of sodium hydroxide(1.5 g) dissolved in 2.8 ml of water was added dropwise to benzyl alcohol (3.76 ml) for 3 minutes. Maintaining the temperature of the reaction mixture below 25° C., epichlorohydrin (III) (2.58 ml) was added dropwise thereto with vigorous stirring for 10 minutes.

After vigorous stirring the reaction liquid at room temperature for 20 hours, 10 ml of water was added, and the mixture extracted with toluene(20 ml). The extract was washed with water(20 ml×4), dried over anhydrous magnesium sulfate, and the solvent was distilled off under reduced pressure, to provide colorless liquid. The crude product was purified by silica gel column chromatography (eluent: n-hexane/ethyl acetate=7/1) to obtain 1.63 g of the desired product as pale yellow liquid.

$^1$H NMR (CDCl$^3$) δ 7.27(m,5H), 4.40(s,2H), 3.77–3.59 (m,1), 3.43–2.97(m,2H), 2.72–2.44(m,2H)

[Method B]

Sodium hydride(60%, 0.65 g) was washed with dried tetrahydrofuran (6 ml×2). Dried tetrahydrofuran (30 ml) was added thereto and the mixture was cooled to 5° C. Glycidol (0.90 ml) was slowly dropped thereto, and the mixture was stirred at the same temperature for 30 minutes.

To the reaction mixture, benzyl bromide (1.6 ml) was slowly dropped, and then the resultant mixture stirred at 5° C. for 30 minutes, and at room temperature overnight as complete the reaction.

After concentrating the reaction mixture under reduced pressure, ethyl acetate (500 ml) was added, and the mixture was washed with water and saturated brine in this order, dried over anhydrous magnesium sulfate. The solvent was distilled off under reduced pressure to provide 2.33 g of crude product as yellow liquid.

The product was used in the next step without further purification.

EXAMPLE 2

Preparation of Monobenzyl Glycerol (V)

To a mixed solvent of water-tetrahydrofuran (1:1, 10 ml), were added glycidyl benzyl ether (1.53 g), and then one drop of concentrated sulfuric acid, and the mixture was stirred under reflux for 4 hours to complete the reaction.

After cooling, the reaction liquid was neutralized with sodium hydroxide and saturated with sodium chloride, and then the mixture was extracted with ethyl acetate (10 ml×6). The extract was dried over anhydrous magnesium sulfate, and the solvent was distilled off under reduced pressure to obtain practically pure product (1.70 g, 100%) as pale yellow oil.

The product was used in the next step without further purification.

IR (neat): 3700–3100 cm$^{-1}$ $^1$H NMR (DMSO-d$_6$) δ 7.33(s,5H), 4.49(s,2H), 3.72–3.45 (m,2H), 3.54–3.23 (m,5H)

EXAMPLE 3

Preparation of 1-O-benzyl-3-O-t-butyl-dimethylsilylglycerol (VT)

To a solution of 1-O-monobenzyl glycerol (1.58 g) in methylene chloride (20 ml), t-butyldimethylsilyl chloride (1.44 g) and then triethylamine (1.33 ml) and N,N-dimethylaminopyridine (0.04 g) were added, and the mixture was stirred overnight at room temperature. Methylene chloride (20 ml) was further added to the reaction liquid, and the mixture was washed with water (20 ml×3) and saturated ammonium chloride (20 ml×3), dried over anhydrous magnesium sulfate. The solvent was distilled off under reduced pressure to obtain pale yellow oil. The product was purified by silica gel column chromatography (eluent: hexane/ethyl acetate=7/1) to obtain the desired product (1.93 g) as pale yellow liquid.

IR (neat): 3600–3100 cm$^{-1}$ $^1$H NMR (CDCl$_3$) δ 7.27(s,5H), 4.50(s,2H), 3.85–3.72 (m,1H), 3.61(d,2H), 3.48(d,2H), 2.55(d,1H), 0.86(s,9H), 0.02(s,6H)

EXAMPLE 4

Preparation of 1-O-benzyl-3-O-t-butyldimethylsilyl-2-O-mesylglycerol (VII)

1-O-benzyl-3-O-t-butyldimethylsilylglycerol (1.63 g) was added to pyridine (6 ml), and the mixture was cooled to 5° C., and mesyl chloride (0.5 ml) was added dropwise thereto, and the resultant mixture was stirred overnight at room temperature. Upon confirming the completion of the reaction, the reaction liquid was cooled to 5° C., water (0.5 ml) was added thereto and the mixture stirred at the same temperature for 30 minutes.

After removing the solvent by evaporation under reduced pressure, the residue was azetroped with toluene (10 ml×3) to completely remove pyridine. To the residue, methylene chloride (20 ml) was added, and the mixture was washed with water (20 ml×3) and 5% hydrochloric acid (20 ml×3) sequentially, dried over anhydrous magnesium sulfate. After removing the solvent by evaporation under reduced pressure, the residue was purified by silica gel column chromatography (eluent: n-hexane/ethyl acetate=7/1) to obtain the desired product (1.66 g) as yellow oil.

$^1$H NMR (CDCl$_3$) δ 7.34(s,5H), 4.78(guintet,1H), 4.57(s, 2H), 3.84(d,2H), 3.72(d,2H), 3.04(s,3H), 0.91(s,9H), 0.09 (s,6H)

EXAMPLE 5

Preparation of 1-O-benzyl-3-O-t-butyldimethylsilyl-2-(ethoxycarbonylmethylthio)glycerol (VIII)

1-O-benzyl-3-O-t-butyldimethylsilyl-2-O-mesylglycerol (0.83 g) was dissolved in N,N-dimethylformamide (5 ml), and ethyl thioglycolate (0.34 ml) and sodium ethoxide (sodium 0.07 g/ethanol 5 ml) were added thereto, and the mixture stirred at 80° C. for 6 hours. After removing the solvent by evaporation under reduced pressure, water was added to the residue and the solution was extracted with ethyl ether (20 ml×3).

The extract was washed with water (20 ml×3) and dried. After removing the solvent by evaporation, the obtained pale brown oil was purified on a silica gel column (eluent: n-hexane/ethyl acetate=10/1) to obtain the desired product (0.50 g) as pale brown oil.

IR (neat): 1725 cm$^{-1}$ $^1$H NMR (CDCl$_3$) δ 7.24(s,5H), 4.46(s,2H), 4.08(q,2H), 3.79(d,2H), 3.64(d,2H), 3.24(s,2H), 3.05(m,1H), 1.18(t,3H), 0.83(s,9H), 0.00(s,6H)

EXAMPLE 6

Preparation of 5-benzyloxymethyl-1,4-oxathian-2-one (X)

[Method A]

Desilylation of 1-O-benzyl-3-O-t-butyldimethylsilyl-2-(ethoxycarbonylmethylthio)glycerol 1-O-Benzyl-3-O-t-butyldimethylsilyl-2-(ethoxycarbonylmethylthio)glycerol (0.37 g) was dissolved in tetrahydrofuran, and 1.0M solution (1.11 ml) of tetra-n-butylammonium fluoride was added thereto. After stirring the mixture at room temperature for 1 hour, the solvent was distilled off under reduced pressure. Methylene chloride (10 ml) was added to the residue, and the mixture was washed with water (10 ml×3) and dried over anhydrous magnesium sulfate. After removing the solvent by evaporation under reduced pressure, pale yellow oil was obtained.

The product was used in the next step without further purification.

IR (neat): 3660–3100, 1720 cm$^{-1}$ $^1$H NMR (CDCl$_3$) δ 7.31(s,5H), 4.53(s,2H), 4.17(q,2H), 3.72(d,2H), 3.64(d,2H), 3.31(s,2H), 3.17(m,1H), 3.00–2.52 (bs,1H), 1.26(t,3H)

Preparation of Lactone (X)

The oily compound obtained above was dissolved in methylene chloride (5 ml), and boron trifluoride (0.1 ml) was added thereto. The mixture was stirred at room temperature for 4 hours. Methylene chloride (10 mol) was further added to the reaction liquid, and the mixture was washed with water (20 ml×3) and dried over anhydrous magnesium sulfate. After removing the solvent by evaporation under reduced pressure, pale brown oil was obtained.

The product was purified on a silica gel column (eluent: n-hexane/ethyl acetate=2/1) to obtain the desired compound (0.14 g) as pale brown oil.

IR (neat): 1740 cm$^{-1}$ $^1$H NMR (CDCl$_3$) δ 7.26(s,5H), 4.47(s,2H), 4.42–4.38 (m,2H), 3.48(d,2H), 3.59–3.44(m,1H), 3.28(d,2H)

[Method B]

Preparation of 1-O-benzyl-2-(carboxymethylthio) glycerol

1-O-Benzyl-3-O-t-butyldimethylsilyl-2-(ethoxycarbonylmethylthio)glycerol (1 g) was added to a solvent mixture of water (8 ml) and methanol (16 ml), and potassium hydroxide (1 g) added thereto and the mixture stirred overnight at room temperature. The reaction mixture was extracted with ethyl ether twice to remove the impurities, and the pH of the extract was adjusted to 1 to 2 with 6N hydrochloric acid. Then the mixture was extracted with ethyl acetate. The extract was dried over anhydrous magnesium sulfate, and the solvent was distilled off under reduced pressure to obtain the desired product (0.6 g).

The product was used in the next step without further purification.

Preparation of Lactone (X)

To a solution of hydroxy acid (0.22 g) obtained above and catalytic amount of N,N-dimethylaminopyridine in methylene chloride (30 ml), a solution of dicyclohexylcarbodiimide (0.21 g) in methylene chloride (1.5 ml) was added dropwise, and the mixture was stirred at room temperature for 30 minutes to complete the reaction. The reaction mixture was filtered to remove urea produced, and the filtrate was concentrated under reduced pressure. The residue was purified on a silica gel column (eluent: n-hexane/ethyl acetate=2/1) to obtain the desired product (0.12 g).

EXAMPLE 7

Preparation of 5-benzyloxymethyl-1,4-oxathian-2-one (XI)

5-Benzyloxymethyl-1,4-oxathian-2-ol (3.42 g) was dissolved in dried methylene chloride (60 ml), and the solution cooled to −78° C. A solution 1.0M diisobutyl aluminum hydride (21.5 ml) was added dropwise thereto for 20 minutes, and the resultant mixture stirred at the same temperature for 30 minutes to complete the reaction. To the reaction mixture, methanol (0.6 ml), saturated sodium sulfate solution (9 ml) and sodium sulfate (4.4 g) were sequentially added, and the mixture was stirred at room temperature for 30 minutes. The residue obtained by concentrating the reaction mixture was extracted with ethyl ether until the product could not be extracted any more with the same solvent. The extract was washed with brine and dried over anhydrous magnesium sulfate, and the solvent was distilled off under reduced pressure, to obtain the desired product (3.47 g) as pale yellow semi-solid.

The product was used in the next step without further purification.

EXAMPLE 8

Preparation of 5-benzyloxymethyl-2-acetoxy-1,4-oxathiane (XII)

5-Benzyloxymethyl-1,4-oxathian-2-ol (3.46 g) was dissolved in pyridine (37 ml), and the solution was cooled to 5° C. Acetic anhydride (3.27 ml) was added dropwise thereto, and the solution was stirred at the same temperature for 4 hours to complete the reaction. After removing the solvent by evaporation under reduced pressure, the residue was azeotroped with toluene to completely remove pyridine to obtain pale brown syrup. The syrup was purified on a silica gel column (eluent: n-hexane/ethyl acetate=3/1) to provide the desired product (2.94 g) as colorless syrup.

$^1$H NMR (CDCl$_3$) δ 7.22(s,5H), 5.89–5.73(m,1H), 4.44 (s,2H), 4.39–3.99(m,2H), 3.65–3.43(m,2H), 2.92–2.72(m, 2H), 2.67–2.58(m,2H), 2.00(s,3H)

EXAMPLE 9

Preparation of N-acetyl-N,O-bis(trimethylsilyl)cytosine

N$^4$-Acetylcytosine (0.82 g) and catalytic amount of ammonium sulfate were added to hexamethyldisilazane (30 ml), and the mixture was stirred under reflux for 2 hours to become a clear solution. Hexamethyldisilazane was distilled off under reduced pressure to obtain the desired product as pale brown oil.

This product was directly used in the condensation reaction.

EXAMPLE 10

Preparation of 1-(5-benzyloxymethyl-1,4-oxathian-2-yl)-N$^4$-acetylcytosine

N$^4$-Acetyl-N,O-bis (tri-methylsilyl)cytosine obtained above was dissolved in 1,2-dichloroethane (30 ml), and a solution of 5-benzyloxymethyl-2-acetoxy-1,4-oxathiane (0.75 g) in 1,2-dichloroethane (15 ml) was added thereto. After cooling the resultant mixture to 5° C., trimethylsilyltriflate (1.0 ml) was added dropwise thereto, and the mixture was stirred at the same temperature for 15 minutes and then at room temperature for 1 hour to complete the reaction. Saturated sodium bicarbonate solution (1 ml) was added thereto, and the mixture was stirred at room temperature for 1 hour and filtered through celite pad. The filtrate was dried over anhydrous magnesium sulfate, and the solvent distilled off under reduced pressure to obtain brown oil.

The crude product was purified on a silica gel column (eluent: chloroform/methanol=20/1) to obtain the desired product (0.55 g) as white foam.

UV λ$_{max}$(MeOH) 300 nm (pH 7)

$^1$H NMR (CDCl$_3$) δ 10.12(bs,1H), 7.85 and 7.62(d each, 1H), 7.46 and 7.42(d each,1H), 7.38–7.27(m,5H), 5.81–5.78 (m,1H), 4.65 and 4.56(d each,2H), 4.53 and 3.46(d each, 2H), 4.21 and 2.99(d each,1H), 3.90 and 3.81(t each,1H), 3.75 and 3.34(m each,1H), 2.70–2.61(m,2H), 2.29(s,3H)

EXAMPLE 11

Preparation of 1-(5-benzyloxymethyl-1,4-oxathian-2-yl]cytosine 1-(5-Benzyloxymethyl-1,4-oxathian-2-yl)-N$^4$-acetylcytosine (0.31 g) was dissolved in methanol (10 ml), and 0.43M sodium methoxide solution (1 ml) was added to the solution. The resultant mixture was stirred at room temperature for one hour to complete the reaction. The reaction mixture was neutralized with acetic acid, and the solvent was removed by evaporation under reduced pressure to obtain pale yellow solid.

The crude product was purified on a silica gel column (eluent: chloroform/methanol=20/1) to provide the desired product (0.24 g) as white solid.

EXAMPLE 12

Preparation of 1-(S-hydroxymethyl-1,4-oxathian-2-yl)cytosine 1-(5-benzyloxymethyl-1,4-oxathian-2-yl)cytosine (0.12 g) was dissolved in methylene chloride (10 ml), and the solution was cooled to −78° C. To the solution, 1M boron trichloride solution (3.7 ml) was added dropwise, and the resultant mixture was stirred at the same temperature for 4 hours. Mixed solvent of methanol-methylene chloride (1/1, 8 ml) was added thereto, and sodium bicarbonate was added to neutralize the reaction mixture. Upon raising the temperature of the reaction mixture to room temperature, the solvent was distilled off under reduced pressure to obtain white solid.

The solid product thus obtained was extracted with methanol three times, and the extract was concentrated under reduced pressure to obtain pale yellow solid. The solid was purified on a silica gel column (eluent: chloroform/methanol=20/1) to obtain the desired product (0.11 g) as pale yellow solid.

$^1$H NMR (MeOH-d$_4$) δ
7.70–7.67(m,1H), 5.91(d,1H), 5.79 and 5.74(dd each,1H), 4.50 and 4.19(dd each,1H), 4.00 and 3.76(t each,1H), 3.54 and 3.31(dd each,2H), 3.83 and 3.18(m each,1H), 2.95 (m, 1H), 2.73 and 2.48(dd each,1H)

EXAMPLE 13

Preparation of N,O-bis(trimethylsilyl)thymine

To hexamethyldisilazane (10 ml), thymine (0.25 g) and ammonium sulfate (catalytic amount) were added, and the mixture was stirred under reflux for 4 hours. When the mixture becomes clear pale yellow solution, hexamethyldisilazane was distilled off under reduced pressure to obtain the desired product as pale brown oil.

The product was directly used in the condensation reaction.

EXAMPLE 14

Preparation of 1-(5-benzyloxymethyl-1,4-oxathian-2-yl)thymine

N,O-Bis(trimethylsilyl)thymine obtained above was dissolved in 1,2-dichloroethane (10 ml), and a solution of 2-acetoxy-5-benzyloxymethyl-1,4-oxathiane (0.27 g) dissolved in 1,2-dichloroethane (15 ml) was added thereto. Upon cooling the resultant mixture to 5° C., trimethylsilyl triflate (0.4 ml) was added dropwise thereto, and the mixture stirred at the same temperature for one hour and then at room temperature overnight.

The reaction mixture was added to a mixed solution of saturated sodium bicarbonate solution (50 ml) and ethyl acetate (50 ml), and the mixture stirred at room temperature for one hour. Upon separating the organic layer, the aqueous layer was further extracted with ethyl acetate (50 ml). The combined organic layer was washed with 5% sodium bicarbonate solution and saturated brine sequentially, and dried over anhydrous magnesium sulfate. After removing the solvent by evaporation under reduced pressure, the remaining dark brown oil was purified on a silica gel column (eluent: chloroform/methanol=20/1) to obtain the desired product (0.14 g) as pale yellow semi-solid.

$^1$H NMR (CDCl$_3$) δ 9.87(bs,1H), 7.37–7.22(m,6H), 5.80–5.75 (pseudo t,1H), 4.66–4.44(m,4H), 3.90–3.40(m, 3H), 2.85–2.44(m,2H), 1.90(d,3H)

EXAMPLE 15

Preparation of 1-(S-hydroxymethyl-1,4-oxathian-2-yl)thymine 1-(5-Benzyloxymethyl-1,4-oxathian-2-yl)thymine (0.14 g) was dissolved in methylene chloride (10 ml), and the solution cooled to −78° C. To the solution, 1M boron trichloride (4.1 ml) was added dropwise, and the mixture stirred at the same temperature for 4 hours. After adding a mixed solution of methanol-methylene chloride (1/1, 8 ml), the temperature of the reaction mixture was raised to room temperature. Upon concentrating the reaction mixture under reduced pressure, the resultant dark brown oil was purified on a silica gel column (eluent: chloroform/methanol=20/1) to obtain the desired product (0.07 g) as pale yellow solid.

$^1$H NMR (DMSO-d$_6$) δ 11.38(bs,1H), 7.60(d,1H), 5.65 and 5.60(dd each,1H), 5.01(t,1H), 4.43 and 4.37(dd each, 1H), 4.02 and 2.63(dd each,1H), 3.94 and 3.07(m each,1H), 3.63 and 3.37(m each,2H), 3.23 and 2.39(m each,2H), 1.77(d,3H)

EXAMPLE 16

Preparation of N,O-bis(trimethylsilyl)-S-chlorouracil

To hexamethyldisilazane (6 ml), 5-chlorouracil(0.42 g) and ammonium sulfate (catalytic amount) were added, and the mixture was stirred under reflux for 2 hours. When the mixture becomes clear solution, hexametihyldisilazane was distilled off under reduced pressure to obtain the desired product as pale brown oil.

The product was directly used in the condensation reaction.

EXAMPLE 17

Preparation of 1-(5-benzyloxymethyl-1,4-oxathian-2-yl)-5-chlorouracil

N,O-Bis(trimethylsilyl)-5-chlorouracil obtained above was dissolved in 1,2-dichloroethane (3.5 ml), and a solution of 2-acetoxy-5-benzyloxymethyl-1,4-oxathiane (0.4 g) dissolved in 1,2-dichloroethane (3.5 ml) was added thereto. Upon cooling the resultant mixture to 5° C., trimethylsilyl triflate (0.3 ml) was added dropwise thereto, and the mixture stirred at the same temperature for 30 minutes, and then the temperature of the reaction mixture raised to room temperature.

The reaction mixture was added to a mixed solution of saturated sodium bicarbonate solution and ethyl acetate, and the mixture was stirred. Upon separating the organic layer, the organic layer was washed with 5% sodium bicarbonate solution, water and brine sequentially, and dried over anhydrous magnesium sulfate. After removing the solvent by evaporation under reduced pressure, the residue was purified on a silica gel column (eluent: chloroform/methanol=30/1) to obtain the desired product (0.49 g) as white solid.

$^1$H NMR (CDCl$_3$) δ 8.69(bs,1H), 7.45–7.26(m,6H), 5.73 (dd,1H), 4.72–4.47(m,4H), 3.93–3.45(m,3H), 2.62–2.70(m, 2H)

EXAMPLE 18

Preparation of 5-chloro-1-(5-hydroxymethyl-1,4-oxathian-2-yl)uracil

5-Chloro-1-(5-benzyloxymethyl-1,4-oxathian-2-yl) uracil (0.42 g) was dissolved in methylene chloride (40 ml), and the solution cooled to −78° C. To the solution, 3M boron trichloride (11.5 ml) was added dropwise, and the mixture stirred at the same temperature for 4 hours. After adding a mixed solution of methanol-methylene chloride (1/1, 14 ml) at room temperature, sodium bicarbonate was added thereto.

Upon stirring and filtering the mixture, the filtrate was concentrated under reduced pressure, and the residue was purified on a silica gel column (eluent: chloroform/methanol=10/1) to obtain the desired product (0.06 g) as white solid.

UV λ$_{max}$ (H$_2$O) 276.2(pH 7), 275.1(pH 2), 274.3(pH 11) nm $^1$H NMR (DMSO-d$_6$) δ 12.01(bs,1H), 8.25(d,1H), 5.75 and 5.71(dd,1H), 5.14(bsr1H), 4.56 and 4.50(d each,1H), 4.13(m, 1H), 3.78–3.72(m,1H), 3.43–3.20(m,2H), 2.77 and 2.53(d each,2H)

EXAMPLE 19

Preparation of K,O-bis(trimethylsilyl)-5-fluorouracil

To hexamethyldisilazane (15 ml), 5-fluorouracil (0.46 g) and ammonium sulfate (catalytic amount) were added, and the mixture was stirred under reflux for 2 hours. When the mixture becomes clear solution, hexamethyldisilazane was distilled off under reduced pressure to obtain the desired product as pale brown oil.

The product was directly used in the condensation reaction.

EXAMPLE 20

Preparation of 1-(5-benzyloxymethyl-1,4-oxathian-2-yl)-5-fluorouracil

N,O-Bis(trimethylsilyl)-5-fluorouracil obtained above was dissolved in 1,2-dichloroethane (10 ml), and a solution of 5-benzyloxymethyl-2-acetoxy-1,4-oxathiane (0.5 g) dissolved in 1,2-dichloroethane (6 ml) was added thereto. Upon cooling the resultant mixture to 5° C., trimethylsilyl triflate (0.3 ml) was added dropwise thereto, and the mixture stirred at the same temperature for 15 minutes, and at room temperature for 20 minutes.

The reaction mixture was added to a mixture of saturated sodium bicarbonate solution and ethyl acetate, and the mixture was stirred. Upon separating the organic layer, the aqueous layer was further extracted with ethyl acetate. The combined organic layer was washed with water and brine sequentially and dried over anhydrous magnesium sulfate. After removing the solvent by evaporation under reduced pressure, the residue was purified on a silica gel column (eluent: chloroform/methanol=25/1) to obtain the desired product (0.56 g) as white foam.

$^1$H NMR (CDCl$_3$) δ 8.89(bs,1H), 7.48 and 7.22(d each, 1H), 5.73 (m,1H), 4.72–4.46(m,3H), 4.16 and 3.77(dd each, 1H), 3.90–3.70(m,1H), 3.45 and 2.80(d each,2H), 3.31 and 2.61(m each 2H)

EXAMPLE 21

Preparation of 5-fluoro-1-(5-hydroxymethyl-1,4-oxathian-2-yl)uracil

5-Fluoro-1-(5-benzyloxymethyl-1,4-oxathian-2-yl)uracil (0.46 g) was dissolved in methylene chloride (50 ml), and the solution cooled to −78° C. To the solution, t-boron trichloride (13.1 ml) was added dropwise, and the mixture stirred at the same temperature for 4 hours. After adding a mixture of methanol-methylene chloride (1/1, 14 ml) and then sodium bicarbonate thereto, the resultant mixture was stirred at room temperature. Upon filtering the mixture to remove solid materials, the filtrate was concentrated, and the residue was purified on a silica gel column chromatography (eluent: chloroform/methanol=15/1) to obtain the desired product (0.11 g) as pale yellow solid.

$^1$H NMR (DMSO-d$_6$) δ 12.05(bs,1H), 8.24(dd,1H), 5.72 (dd,1H), 5.14(t, 1H), 4.54 and 4.22(m each,2H), 3.73(m, 1H), 3.33(m,1H), 2.78–2.54(m,2H)

EXAMPLE 22

Preparation of trimethylsilyl-2-amino-6-chloropurine

To hexamethyldisilazane (8 ml), 2-amino-6-chloropurine (0.25 g), ammonium sulfate (catalytic amount) and trimethylsilyl chloride (catalytic amount) were added, and the mixture was stirred under reflux for 4 hours. When the mixture becomes clear solution, hexamethyldisilazane was distilled off under reduced pressure to obtain the desired product as pale brown oil.

The product was directly used in the condensation reaction.

EXAMPLE 23

Preparation of 9-(5-benzyloxymethyl-1,4-oxathian-2-yl)-2-amino-6-chloropurine

Trimethylsilyl-2-amino-6-chloropurine obtained above was dissolved in 1,2-dichloroethane (5 ml), and a solution of 5-benzyloxymethyl-2-acetoxy-1,4-oxathiane (0.2 g) dissolved in 1,2-dichloroethane (10 ml) was added thereto. Upon cooling the resultant mixture to 5° C., trimethylsilyl triflate (0.29 ml) was added drop-wise thereto, and the mixture stirred at the same temperature for 30 minutes, and under reflux for an hour.

The reaction mixture was added to a mixture of saturated sodium bicarbonate solution and ethyl acetate, and the mixture was stirred. Separated organic layer was washed with 5% sodium bicarbonate solution, water and brine sequentially and dried over anhydrous magnesium sulfate. After removing the solvent by evaporation under reduced pressure, the residue was purified on a silica gel column (eluent: chloroform/methanol=50/1) to obtain the desired product (0.05 g) as pale yellow syrup.

UV λ$_{max}$(methanol) 310.7 nm $^1$H NMR (DMSO-d$_6$) δ 8.36(d,1H), 7.36(m,5H), 7.02(bs, 2H), 5.72(m,5H), 4.55(d,2H), 4.41–4.01(m,2H), 3.76–3.46 (m,3H), 3.01–2.65(m,2H)

EXAMPLE 24

Preparation of 2-amino-6-chloro-9-(5-hydrozymethyl-1,4-oxathian-2-yl)purine 9-(5-Benzyloxymethyl-1,4-oxathian-2-yl)-2-amino-6-chloropurine (0.03 g) was dissolved in methylene chloride (6 ml), and the solution cooled to −78° C. To the solution, 1M boron trichloride (0.9 ml) was added dropwise, and the mixture stirred at the same temperature for 5 hours. After adding a mixture of methanol-methylene chloride (1/1, 6 ml) and then sodium bicarbonate thereto, the resultant mixture was stirred at room temperature. Upon filtering the mixture, the filtrate was concentrated under reduced pressure, and the residue was purified on a silica gel column (eluent: chloroform/methanol=20/1) to obtain the desired product (0.01 g) as pale yellow solid.

UV λ$_{max}$(methanol) 309 nm $^1$H NMR (DMSO-d$_6$) δ 8.38(d,1H), 7.03(bs,2H), 5.65(m, 1H), 5.04(t,1H), 4.40(m,1H), 3.63(m,2H), 2.90–2.82(m,2H)

EXAMPLE 25

Preparation of 9-(S-hydroxymethyl-1,4-oxathian-2-yl)guanine

2-Amino-6-chloro-9-(5-hydroxymethyl-1,4-oxathian-2-yl)purine (0.03 g) was dissolved in methanol (10 ml), and 2-mercaptoethanol (0.03 ml) and 1M, sodium methoxide solution (0.01 ml) were added thereto. The resultant mixture was stirred under reflux for three days. After concentrating the reaction mixture under reduced pressure, water was added thereto, and the aqueous layer was washed several times with ethyl ether. Acetic acid was added thereto to adjust pH of the aqueous layer to 7, and the solvent was distilled off under reduced pressure. The residue was purified on a silica gel column (eluent: chloroform/methanol= 5/1) to obtain the desired product (0.02 g) as pale yellow solid.

UV λ$_{max}$ (H$_2$O): 252, 270 nm(sh) (pH7); 255,275 nm(sh) (pH2); 260(sh), 267 nm(pH11)

$^1$H NMR (DMSO-d$_6$) δ 7.89 and 7.68(d each,1H), 6.74 (bs,2H), 5.58(m, 1H), 4.76(t,1H), 4.41–4.15(m,2H), 3.70–3.51(m,3H), 2.91–2.87(dd,2H)

EXAMPLE 26

Preparation of 1-O-benzyl-3-O-t-butyldimethylsilyl-2-O-ethoxycarbonylmethylglycerol (XIII)

Dried tetrahydrofuran (600 ml) was added to 60% sodium hydride (5.8 g), and the solution cooled to 5° C. A solution (100 ml) of 1-O-benzyl-3-O-t-butyldimethylsilylglycerol (35.9 g) in tetrahydrofuran was added thereto, and the resultant mixture stirred at the same temperature for 2 hours. Then, ethyl bromoacetate (24.3 g) was added dropwise thereto, and the mixture stirred at the same temperature for 2 hours and then room temperature overnight. Upon concentrating the reaction mixture under reduced pressure, water was added to the residue, and the mixture was acidified with 5% hydrochloric acid. After extracting the aqueous layer with ethyl acetate, the extract was washed with saturated brine and dried over anhydrous magnesium sulfate. Upon concentrating thereof under reduced pressure, the residue was purified on a silica gel column (eluent: n-hexane/ethyl acetate=6/1) to obtain the desired product (28.7 g) as oil.

IR (neat): 1745 and 1725 cm$^{-1}$ $^1$H NMR (CDCl$_3$) δ 7.27(s,5H), 4.50(s,2H), 4.27(s,2H), 4.20–4.00(m,2H), 3.74–3.50(m,5H), 1.21(t,31), 0.85(s,9H), 0.00(s,6H)

EXAMPLE 27

Preparation of 1-O-benzyl-2-O-carboxymethylglycerol (XIV)

1-O-Benzyl-3-t-butyldimethylsilyl-2-O-carboxymethylglycerol (5 g) was dissolved in methanol (50 ml), and a solution of 85% potassium hydroxide (7 g) in water (50 ml) was added thereto. The mixture was stirred at room temperature for 60 hours to complete the reaction.

After removing methanol by concentrating the resultant mixture under reduced pressure, the residue was washed by ether and acidified with 6N hydrochloric acid, and extracted with ethyl acetate. The extract was washed with saturated brine and dried over anhydrous magnesium sulfate. Upon concentrating the organic layer under reduced pressure, the desired product (2.7 g) was obtained as oil.

This product was used directly in the next step without further purification.

IR (neat): 3500–2800, 1720 cm$^{-1}$

EXAMPLE 28

Preparation of 5-benzyloxymethyl-2-oxo-1,4-dioxane (XV)

Hydroxy acid (2.34 g) obtained from Example 27 was dissolved in benzene (400 ml), and concentrated sulfuric acid (4 drops) was added thereto. The reaction mixture was stirred under reflux for 2 hours as removing water by Dean-Stark trap to complete the reaction. The reaction mixture was washed with water and saturated brine sequentially and dried over anhydrous magnesium sulfate. Upon concentrating the reaction mixture under reduced pressure, lactione (2 g) was obtain as oil.

This product was used in the next step without further purification.

$^1$H NMR (CDCl$_3$) δ 7.32(s,5H), 4.66–4.16(m,7H), 3.65–3.42 (m,2H)

EXAMPLE 29

Preparation of 5-benzyloxymethyl-2-acetoxy-1,4-dioxane (XVII)

5-Benzyloxymethyl-2-oxo-1,4-dioxane (2 g) was dissolved in methylene chloride (70 ml), and the solution cooled to −78° C. To the solution, 1M diisobutyl aluminum hydride solution (13.7 ml) was added dropwise, and the mixture stirred at the same temperature for 30 minutes to complete the reaction.

After adding methanol (0.9 ml), the temperature of the reaction mixture was raised to room temperature. After adding saturated sodium sulfate solution and sodium sulfate (2.8 g), the mixture was stirred at room temperature for 10 minutes. The residue obtained by concentrating the reaction mixture under reduced pressure was extracted several times with ether. The combined extract was concentrated under reduced pressure, and pyridine (20 ml) was added to the oily compound obtained. Acetic anhydride (2 ml) was added thereto, and the mixture stirred at 5° C. for 5 hours, and at room temperature overnight.

Upon concentrating the reaction mixture under reduced pressure, the residue was purified on a silica gel column (eluent: n-hexane/ethyl acetate=2/1) to obtain the desired product (1.81 g) as pale yellow oil.

$^1$H NMR (CDCl$_3$) δ 7.33(s,5H), 5.95–5.71(m,1H), 4.55 (s,2H), 4.02–3.38(m,7H), 2.14 and 2.10(s,each,3H)

EXAMPLE 30

Condensation of Silylated Base With Sugar (General Procedure)

Pyrimidine or purine base (2 mmole) was suspended in hexamethyldisilazane, and ammonium sulfate (catalytic amount) was added thereto. The mixture was stirred under reflux for 2 hours. After removing hexamethyldisilazane under reduced pressure, 1,2-dichloroethane (2.5 ml) and a solution of 5-benzyloxymethyl-2-acetoxy-1,4-dioxane (1 mmole) in 1,2-dichloroethane (2.5 ml) were sequentially added to the residue, and the mixture cooled to 5° C. Trimethylsilyl triflate (2 mmole) was added dropwise thereto, and the reaction mixture was stirred at 5° C. for 1 hour to complete the reaction.

The reaction mixture was added to a mixture of saturated sodium bicarbonate solution and ethyl acetate. Upon separating the organic layer, the aqueous layer was further extracted with ethyl acetate. The combined organic layer was washed with saturated sodium bicarbonate solution, water and saturated brine sequentially, dried over anhydrous magnesium sulfate. Upon concentrating the reaction mixture under reduced pressure, the residue was purified on a silica gel column (eluent: chloroform/methanol=20/1) to obtain the condensation product.

EXAMPLE 31

Preparation of 1-(5-benzyloxymethyl-1,4-dioxan-2-yl)-N$^4$-acetylcytosine

In accordance with the same procedure as Example 30, the desired product (yield: 70%) was obtained as white solid.

$^1$H NMR (CDCl$_3$) δ 9.62(s,1H), 7.80(d,1H), 7.40(d,1H), 7.28(s,5H), 5.90–5.70(m,1H), 4.50(s,2H), 3.30–4.30(m,7H), 2.22(s,3H)

EXAMPLE 32

Preparation of 1-(5-benzyloxymethyl-1,4-dioxan-2-yl)thymine

In accordance with the same procedure as Example 30, the desired product was obtained quantitatively as white solid.

UV λ$_{max}$(MEOH) 263.2 nm (pH 7)
$^1$H NMR (CDCl$_3$) δ 9.88(bs,1H), 7.43(d,1H), 7.26(s,5H), 5.90–5.60(m,1H), 4.48(s,2H), 4.20–3.20(m,7H)

EXAMPLE 33

Preparation of 1-(5-benzyloxymethyl-1,4-dioxan-2-yl)-N$^4$-fluorouracil

In accordance with the same procedure as Example 30, the desired product was obtained quantitatively as white solid.

UV λ$_{max}$(MeOH) 265.2 nm (pH 7)
$^1$H NMR (CDCl$_3$) δ 9.88(bs,1H), 7.43(d,1H), 7.26(s,5H), 5.90–5.60(m,1H), 4.48(s,2H), 4.20–3.20(m,7H)

EXAMPLE 34

Preparation of 1-(5-benzyloxymethyl-1,4-dioxan-2-yl)-5-iodouracil

In accordance with the same procedure as Example 30, the desired product was obtained quantitatively as white solid.

UV λ$_{max}$(MeOH) 285.0 nm (pH 7)
$^1$H NMR (CDCl$_3$) δ 8.65(s,1H), 7.85(s,1H), 7.34(s,5H), 5.90–5.60(m,1H), 4.56(s,2H), 4.20–3.30(m,7H)

EXAMPLE 35

Preparation of 9-(5-benzyloxymethyl-1,4-dioxan-2-yl)-2-amino-6-chloropurine

The desired product (yield: 45%) was obtained as white solid in accordance with the same procedure as Example 30 except that the reaction was stirred under reflux.

$^1$H NMR (CDCl$_3$) δ 7.94(s,1H), 7.34(s,5H), 5.90–5.70 (m,1H), 4.58(s,2H), 4.40–3.40(m,7H)

EXAMPLE 36

Debenzylation of Condensation Product (General Procedure)

The condensation product (1 mmole) was dissolved in methylene chloride (30 ml), and the solution cooled to −78°

C. To the solution, 1M boron trichloride (10 mmole) was added dropwise, and the mixture stirred at the same temperature for 4 hours to complete the reaction. After adding a mixture of methanol and methylene chloride (1/1, 12 ml), the reaction temperature was raised to room temperature. Sodium bicarbonate was added to neutralize the reaction mixture, and the reaction mixture filtered. Upon concentrating the filtrate under reduced pressure, the residue was purified on silica gel column (eluent: chloroform/methanol= 10/1) to obtain the desired product.

EXAMPLE 37

Preparation of 1-(5-hydroxymethyl-1,4-dioxan-2-yl) cytosine

In accordance with the same procedure as Example 36, the desired product (yield: 36%) was obtained as white solid starting from 1-(5-benzyloxymethyl-1,4-dioxan-2-yl) cytosine.

UV $\lambda_{max}$ (H$_2$O) 267.8(pH 7), 276.4(pH 2), 268.2(pH 11) nm $^1$H NMR (DMSO-d$_6$) δ 7.98(d,1H), 7.27(d,2H), 5.70(d, 1H), 5.80–5.60(m,1H), 4.90–4.70(m,1H), 4.00–3.20(m,7H)

EXAMPLE 38

Preparation of 1-(5-hydroxymethyl-1,4-dioxan-2-yl) thymine

Starting from 1-(5-hydroxymethyl-1,4-dioxan-2-yl)-thymine, desired product (yield:42%) was obtained as white solid in accordance with the same procedure as Example 36.

UV $\lambda_{max}$(H$_2$O) 264.6(pH 7), 266.4(pH 2), 264.0(pH 11) nm $^1$H NMR (DMSO-d$_6$) δ 11.42(s,1H), 7.59(s,1H), 5.55(dd, 1H), 4.84(t,1H), 4.10–3.20(m,7H), 1.78(s,3H)

EXAMPLE 39

Preparation of 5-fluoro-1-(5-hydroxymethyl-1,4-dioxan-2-yl)uracil

Starting from 1-(5-benzyloxymethyl-1,4-dioxan-2-yl)-5-fluorouracil, desired product (yield:17%) was obtained as white solid in accordance with the same procedure as Example 36.

UV $\lambda_{max}$(H$_2$O) 266.8(pH 7), 266.4(pH 2), 267.8(pH 11) nm $^1$H NMR (DMSO-d$_6$) δ 12.00(bs,1H), 8.20–8.00(m,1H), 5.80–5.50(m,1H), 4.85(bs,1H), 4.10–3.20(m,7H)

EXAMPLE 40

Preparation of 5-iodo-1-(5-hydroxymethyl-1,4-dioxan-2-yl)uracil

Starting from 1-(5-benzyloxymethyl-1,4-dioxan-2-yl)-5-iodouracil, desired product (yield:77%) was obtained as white solid in accordance with the same procedure as Example 36.

UV $\lambda_{max}$ (H$_2$O) 286.0(pH 7), 285.4(pH 2), 277.2(pH 11) nm

EXAMPLE 41

Preparation of 2-amino-6-chloro-9-(5-hydroxymethyl-1,4-dioxan-2-yl)purine

Starting from 1-(5-benzyloxmethyl-1,4-dioxan-2-yl)-2-amino-6-chloropurine, desired product (yield:78%) was obtained as white solid in accordance with the same procedure as Example 36.

UV $\lambda_{max}$(H$_2$O) 308.4(pH 7), 306.2(pH 2), 306.6(pH 11) nm $^1$H NMR (DMSO-d$_6$) δ 8.44 and 8.33(s each,1H), 7.08 and 7.05(s each,2H), 5.90–5.45(m,1H), 4.88(m,1H), 4.40–3.20(m,7H)

EXAMPLE 42

Preparation of 1-(5-benzyloxynethyl-1,4-dioxan-2-yl) cytosine

Methanol (5 ml) was added to 1-(5-benzyloxymethyl-1,4-dioxan-2-yl)-N$^4$-acetylcytosine (13.9 mg) to dissolve the compound, and catalytic amount of sodium methoxide was added thereto, and the resultant mixture was stirred at room temperature for 30 minutes to complete the reaction. After neutralizing the reaction mixture by adding acetic acid, the mixture was concentrated under reduced pressure to obtain the desired product (0.12 g) as white solid.

The product is used in the next step without further purification.

UV $\lambda_{max}$(MeOH) 270.6(pH 7) nm

EXAMPLE 43

Preparation of 9-(5-hydroxymethyl-1,4-dioxan-2-yl) guanine

Methanol (20 ml) was added to 2-amino-6-chloro-9-(5-hydroxymethyl-1,4-dioxan-2-yl)purine (0.2 g) to dissolve the compound, and 2-mercaptoethanol (0.12 ml) and 1M sodium methoxide (1.62 ml) were added thereto, and then the resultant mixture was stirred under reflux for 10 hours.

To the residue obtained by concentrating the reaction mixture under reduced pressure, water (10 ml) was added, and the aqueous layer was washed with ether and neutralized. The resultant solution was stood in a refrigerator, and then the precipitated solid was filtered to obtain the desired product (0.03 g) as white solid.

UV $\lambda_{max}$(H$_2$O) 251.8(pH 7), 254.2(pH 2), 265.2(pH 11) nm $^1$H NMR (DMSO-d$_6$) δ 10.80(bs,1H), 8.07 and 7.87(s each,1H), 6.61 (d,2H), 5.78–5.42(m,1H), 4.83(bs,1H), 4.21–3.36(m,7H)

EXAMPLE 44

Preparation of diethyl 3,3-dimethoxypropylmalonate (XIV)

Sodium (0.63 g) was added to ethanol (4 ml), and the mixture was stirred until the sodium being completely dissolved. Diethyl malonate was added thereto at room temperature, and the resultant mixture stirred.

3-Bromopropionaldehyde dimethyl acetal was added thereto, and the mixture stirred at room temperature for two hours and then under reflux for further 2 hours to complete the reaction. After concentrating the reaction mixture under reduced pressure, ethyl acetate (30 ml) and water (30 ml) were added thereto, and the mixture was neutralized with 5% hydrochloric acid. Separated organic layer was dried over anhydrous magnesium sulfate, and the solvent was distilled off under reduced pressure. The residue was purified on a silica gel column (eluent: n-hexane/ethyl acetate= 7/1) to obtain the desired product (9.28 g, 65%) as pale yellow oil.

IR (neat) cm$^{-1}$ :1720
$^1$H NMR (CDCl$_3$) δ 4.29(t,1H), 4.12(q,4H), 3.20(s,6H), 1.96–1.80(m,2H), 1.61–1.50(m,2H), 1.18(t,6H)

EXAMPLE 45

Preparation of 5,5-dimethoxy-2-hydroxymethylpentanol (XX)

Diethyl 3,3-dimethoxypropylmalonate (7.4 g) and sodium borohydride (1.47 g) were added to tert-butyl alcohol (50 ml), and methanol (3.1 ml) was added at three portions over 30 minutes while stirring under reflux. The reaction mixture was further stirred under reflux for 1 hour to complete the reaction.

After cooling, the reaction mixture was neutralized with 6N hydrochloric acid and filtered. The filtrate was concentrated under reduced pressure, and the residue was extracted several times with ethanol. The combined extract was concentrated under reduced pressure, and the residue purified on a silica gel column (eluent: chloroform/methanol=15/1) to obtain the desired product (3.93 g, 75%) as pale yellow oil.

IR (neat) cm$^{-1}$: 3400
$^1$H NMR (DMSO-d$_6$) δ 4.31(m,3H), 3.37–3.32(m,6H), 3.20(s,6H), 1.57–1.36(m,3H), 1.28–1.17(m,2H)

EXAMPLE 46

Preparation of 2-methoxy-5-hydroxymethyltetrahydropyran (XXI)

5,5-Dimethoxy-2-hydroxymethylpentanol (2.87 g) was dissolved in tetrahydrofuran, and 1N hydrochloric acid (0.1 ml) was added dropwise thereto, and then the mixture stirred at room for 4 hours. After concentrating the reaction mixture, the residue was purified on a silica gel column (eluent: chloroform/methanol=20/1) to obtain the desired product (2.07 g, 88%) as pale yellow oil.

IR (neat) cm$^{-1}$: 3400
$^1$H NMR (DMSO-d$_6$) δ 4.56–4.26, 3.91–3.84 and 3.57–3.50(m,2H), 3.39–3.14(m,7H), 1.73–1.24(m,5H)

EXAMPLE 47

Preparation of 2-methoxy-5-acetoxymethyltetrahydropyran (XXII)

2-Methoxy-5-hydroxymethyltetrahydropyran (0.91 g) was dissolved in pyridine (10 ml), and the solution cooled to 5° C. Acetic anhydride (3.15 ml) was added thereto, and the mixture stirred at the same temperature For 1 hour, and then at room temperature overnight. After removing pyridine by evaporation under reduced pressure, the residue was purified on a silica gel column (eluent: n-hexane/ethyl acetate=½) to obtain the desired product (0.93 g, 80.0%) as pale yellow oil.

IR (CHCl$_3$) cm$^{-1}$: 1730
$^1$H NMR (CDCl$_3$) δ 4.56 and 4.35(m each,1H), 4.00–3.83 (m,2H), 3.30(d,2H), 3.24(s,3H), 2.01(s,3H), 1.79–1.32(m, 5H)

EXAMPLE 48

Preparation of 1-(5-acetoxymethyltetrahydropyran-2-yl)-N$^4$-acetylcytosine

N$^4$-Acetyl-N,O-bis(trimethylsilyl)cytosine was dissolved in 1,2-dichloroethane (10 ml). A solution of 2-methoxy-5-acetoxymethyltetrahydropyran (0.2 g) in 1,2-dichloroethane (5 ml) was added thereto, and the mixture cooled to 5° C. Trimethylsilyltriflate (0.41 ml) was added dropwise thereto, and the mixture was stirred at the same temperature for 30 minutes and at room temperature for an hour to complete the reaction. The reaction mixture was added to a mixture of saturated sodium bicarbonate solution (10 ml) and ethyl acetate (10 ml), and the resultant mixture was stirred at room temperature. Separated organic layer was dried over anhydrous magnesium sulfate and concentrated. The residue was purified on a silica gel column (eluent: chloroform/methanol=35/1) to obtain the desired product (0.34 g) as pale yellow solid.

UV $\lambda_{max}$(MeOH) 246.5, 297.6 nm
$^1$H NMR (CDCl$_3$) δ 10.89(s,1H), 7.99(d,1H), 7.22(d,1H), 5.57(m,1H), 4.09–3.85(m,2H), 3.48–3.15(m,2H), 2.09(s, 3H), 2.04 (s,3H), 1.74–1.30(m,4H)

EXAMPLE 49

Preparation of 1-(5-hydroxymethylhydropyran-2-yl) cytosine 1-(5-Acetoxymethyltetrahydropyran-2-yl)-N$^4$-acetylcytosine (0.21 g) was dissolved in methanol (6 ml), and catalytic amount of sodium methoxide solution was added thereto. The resultant mixture was stirred at room temperature for 5 hours to complete the reaction. The reaction mixture was neutralized by acetic acid, and the solvent was distilled off under reduced pressure. The residue was recrystallized from water-methanol solution to obtain the desired product (0.04 g, 28%) as white solid.

UV $\lambda_{max}$(H$_2$O) 271.2(pH 7), 279.0(pH 2), 270.6(pH 11) nm
$^1$H NMR (DMSO-d$_6$) δ 7.47(d,1H), 7.18(bs,2H), 5.74(d, 1H), 5.53(t,1H), 4.32(t,1H), 3.34–3.25(m,4H), 1.80–1.10(m, 5H)

EXAMPLE 50

Preparation of 1-(5-acetoxymethyltetrahydropyran-2-yl)thymine

After dissolving N,O-bis(trimethylsilyl)thymine in 1,2-dichloroethane (5 ml), a solution of 2-methoxy-5-acetoxymethyltetrahydropyran (0.10 g) in 1,2-dichloroethane (5 ml) was added thereto. The resultant mixture was cooled to 5° C., and trimethylsilyl triflate (0.24 g) was added dropwise thereto. The mixture was stirred at the same temperature for 4 hours to complete the reaction.

The reaction mixture was poured into a mixture of saturated sodium bicarbonate (10 ml) and ethyl acetate (10 ml), and the resultant mixture was stirred at room temperature for 30 minutes. After extracting the mixture, the organic layer was washed with 5% sodium bicarbonate solution and saturated brine sequentially, and dried over anhydrous magnesium sulfate. After concentration, the residue was purified on a silica gel column (eluent: chloroform/methanol=20/1) to obtain the desired product (0.086 g, 60.4%) as pale yellow oil.

UV $\lambda_{max}$(MeOH) 264.7 nm
$^1$H NMR(DMSO-d$_6$) δ 11.32(s,1H), 7.57(s,1H), 5.46(m, 1H), 3.98–3.77(m,4H), 2.04(s,3H), 1.78(s,3H), 2.02–1.46 (m,5H)

EXAMPLE 51

Preparation of 1-(5-hydroxymethyltetrahydropyran-2-yl)thymine 1-(5-Acetoxymethyltetrahydropyran-2-yl)thymine (0.07 g) was dissolved in a saturated ammonia solution in methanol, and the mixture stirred overnight. After removing the solvent by evaporation under reduced pressure from the mixture, the residue was purified on a silica gel column (eluent: chloroform/methanol=15/1) to obtain the desired product (0.032 g, 52%) as white solid.

UV $\lambda_{max}$(H$_2$O) 266.1(pH 7), 265.7(pH 2), 264.9(pH 11) nm $^1$H NMR (DMSO-d$_6$) δ 11.30(s,1H), 7.56(s,1H), 5.44–5.39(m,1H), 4.56(t,1H), 3.35–3.19(m,4H), 1.92–1.12 (m,5H), 1.71 (s,3H)

EXAMPLE 52

Preparation of N$^2$-Acetylguanine

Guanine (10.1 g) was suspended in N,N-dimethylacetamide (100 ml), and acetic anhydride (20 ml) was added thereto. The mixture was stirred under reflux for 2 hours and filtered hot. After cooling the filtrate to room temperature, the solid precipitated was filtered, and the solid suspended in ethanol (66 ml). After stirring 1.5 hours, the suspension was filtered. The solid thus obtained was stirred under reflux in 50% ethanol for 3 hours, and the solution cooled. The solid product thus obtained was filtered, washed with 50% ethanol, and dried to provide the desired product (9.36 g, 72.7%) as white solid.

$^1$H NMR (DMSO-d$_6$) δ 13.14(bd,1H), 12.14(bs,1H), 11.67(bs,1H), 8.10 (bs,1H), 2.28(s,3H)

EXAMPLE 53

Preparation of 9-(5-acetoxymethyltetra hydropyran-2-yl)-N$^2$-acetylguanine and 7-(5-acetoxymethyltetrahydropyran-2-yl)-N$^2$-acetylguanine N$^2$-Acetylguanine (0.39 g) was silylated according to a conventional method, and the silylated compound was dissolved in 1,2-dichloroethane (15 ml). A solution of 2-methoxy-5-acetoxymethyltetrahydropyran (0.19 g) dissolved in 1,2-dichloroethane5(5 ml) was added thereto. Then, trimethylsilyltriflate (0.39 ml) was added dropwise to the mixture and the resultant mixture stirred overnight.

To the reaction mixture, saturated sodium bicarbonate solution (20 ml) and dichloromethane (20 ml) were added, and the mixture stirred for 30 minutes. The organic layer was separated and the aqueous layer was extracted several times. The combined organic layer was dried over anhydrous magnesium sulfate, and then concentrated. The residue was purified on a silica gel column (eluent: chloroform/methanol=40/1) to obtain N$_9$ isomer (80 mg, 21%) and N$_7$ isomer (52 mg, 14%), respectively as colorless oil.

UV $\lambda_{max}$(MeOH) 257, 280 nm (sh): N$_9$ isomer 264, 280 nm (sh): N$_7$ isomer

EXAMPLE 54

Preparation of 9-(5-hydroxymethyltetrahydropyran-2-yl)guanine 9-(5-Acetoxymethyltetrahydropyran-2-yl)-N$^2$-acetylguanine (80 mg) was dissolved in dried methanol, and catalytic amount of sodium methoxide was added thereto. After stirring at room temperature overnight, the mixture was neutralized with methanolic hydrochloric acid and concentrated under reduced pressure. The residue was purified on a silica gel column (eluent: chloroform/methanol= 7/1) to obtain the desired product (45 mg, 73%) as pale gray solid.

UV $\lambda_{max}$(H$_2$O) 250.0(pH 7), 253.2(pH 2), 263.7(pH 11) nm $^1$H NMR(DMSO-d$_6$) δ 10.75(s,1H), 7.87(s,1H), 6.63(s, 2H), 5.27(m,1H), 4.63(t,1H), 4.10–3.23(m,4H), 1.91–1.72 (m,5H)

EXAMPLE 55

Preparation 7-(5-hydroxymethyltetrahydropyran-2-yl)guanine 7-(5-Acetoxymethyltetrahydropyran-2-yl)-N$^2$-acetylguanine (52 mg) was deacetylated in accordance with the same method as Example 54, and the product recrystallized from methanol to provide the desired product (39 mg, 36%) as white solid.

UV $\lambda_{max}$(H$_2$O) 283.0(pH 7), 248.6(pH 1), 281.4(pH 11) nm $^1$H NMR (DMSO-d$_6$) δ 10.94(s,1H), 8.16(s,1H), 6.24(s, 2H), 5.71(m,1H), 4.61(t,1H), 4.02–3.33(m,4H), 2.21–1.80 (m,5H)

EXAMPLE 56

Anti-HBV Effect

Anti-HBV effect of 1-(5-hydroxymethyl-1,4-dioxan-2-yl) thymine, one of the desired product of the present invention prepared in Example 38, was tested in HepG2 2. 2. 15 cell line. The resultant Effective Concentration (Ec$_{50}$, EC$_{90}$), Cytotoxic Concentration (CC$_{50}$) and Selectivity Index (SI) are shown in the Table below.

TABLE 1

| | Anti-HBV effect | | | |
|---|---|---|---|---|
| Test Compound | EC$_{50}$ (μg/ml) | EC$_{90}$ (μg/ml) | CC$_{50}$ (μg/ml) | SI (CC$_{50}$/EC$_{50}$) |
| Compound of Ex.38 | 4.5 | 15 | 846 | 188 |

As shown in the Table above, the compound of the present invention has excellent anti-HBV effect.

What is claimed is:

1. A nucleoside of formula I

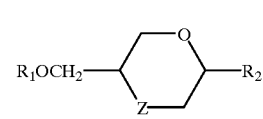

or a pharmaceutically acceptable salt thereof, wherein:

R$_1$ is hydrogen;

R$_2$ is selected from the group consisting of

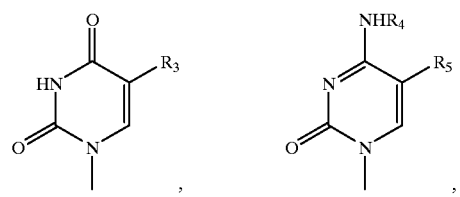

-continued

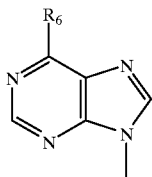
and
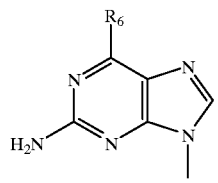

wherein R₃ is hydrogen, or a methyl, fluoro, chloro, bromo, iodo, trifluoromethyl, methoxymethyl or 2-bromovinyl group, R₄ is hydrogen or an acetyl group, R₅ is hydrogen, or a fluoro or methyl group, and R₆ is a hydroxy, chloro or amino group; and Z is S, SO, SO₂, or C.

2. An anti-HBV composition comprising:

(i) a nucleoside of formula I

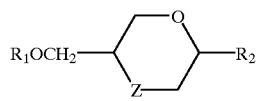

or a pharmaceutically acceptable salt thereof, wherein:

R₁ is hydrogen;

R₂ is selected from the group consisting of

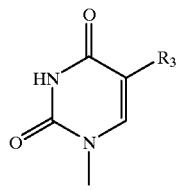
,
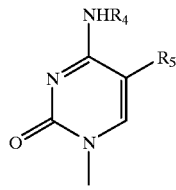
,

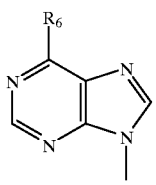
and
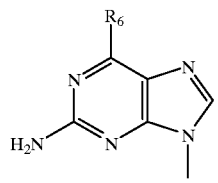

wherein R₃ is hydrogen, or a methyl, fluoro, chloro, bromo, iodo, trifluoromethyl, methoxymethyl or 2-bromovinyl group, R₄ is hydrogen or an acetyl group, R₅ is hydrogen, or a fluoro or methyl group, and R₆ is a hydroxy, chloro or amino group; and Z is S, SO, SO₂ or C; and (ii) a pharmaceutically acceptable carrier.

3. A process for the preparation of a compound of formula I

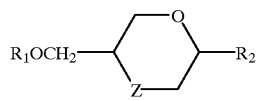

or a pharmaceutically acceptable salt thereof, wherein:

R₁ is hydrogen;

R₂ is selected from the group consisting of

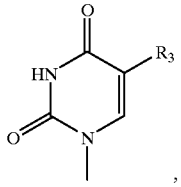
,
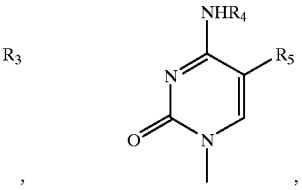
,

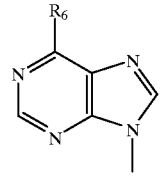
and
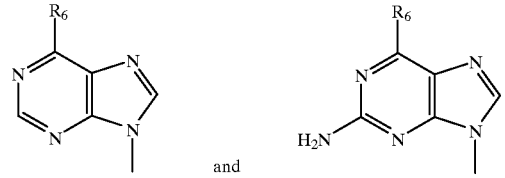

wherein R₃ is hydrogen, or a methyl, fluoro, chloro, bromo, iodo, trifluoromethyl, methoxymethyl or 2-bromovinyl group, R₄ is hydrogen or an acetyl group, R₅ is hydrogen, or a fluoro or methyl group, and R₆ is a hydroxy, chloro or amino group; and Z is S, SO, SO₂, O or C, which comprises the step of reacting a compound of Formula II $$R_7OCH_2 \cdots \overset{O}{\underset{Z}{\diagdown}} \cdots L \quad \text{II}$$

wherein R₇ is hydrogen or a hydroxy-protecting group, L is RCO₂, wherein R is a C₁–C₆ alkyl, or a C₆–C₁₂ aromatic group, a halide or an alkoxy group, and Z is defined as above, with base of the formula R₂H, wherein R₂ is defined as above, in the presence of Lewis Acid.

4. A nucleoside or a pharmaceutically acceptable salt thereof according to claim 1, wherein Z is S, SO or SO₂.

5. A nucleoside or a pharmaceutically acceptable salt thereof according to claim 1, wherein Z is C.

6. A nucleoside or a pharmaceutically acceptable salt thereof according to one of claims 1, 4 and 5, wherein:

R₂ is selected from the group consisting of uracil-1-yl, thymine-1-yl, 5-fluoro-uracil-1-yl, 5-chlorouracil-1-yl, 5-bromouracil-1-yl, 5-iodouracil-1-yl, cytosin-1-yl, 5-methylcytosin-1-yl, 5-flurocytonsin-1-yl, 6-hydroxypurin-9-yl, purin-9-yl, 2,6-diaminopurin-9-yl, 2-amino-6-chloropurin-9-yl and guanin-9-yl.

7. A nucleoside derivative or a pharmaceutically acceptable salt thereof according to claim 4 selected from the group consisting of 1-(5-hydroxymethyl-1,4-oxathian-2-yl)cytosine. 5-fluoro-1-(5-hydroxymethyl-1,4-oxathian-2-yl)cytosine, 5-methyl-1-(5-hydroxymethyl-1,4-oxathian-2-yl)cytosine, 1-(5-hydroxymethyl-1,4-oxathian-2-yl)thymine, 5-iodo-1-(5-hydroxymethyl-1,4-oxathian-2-yl)uracil, 5-bromo-1-(5-hydroxymethyl-1,4-oxathian-2-yl) uracil, 5-chloro-1-(5-hydroxymethyl-1,4-oxathian-2-yl)uracil, 5-fluoro-1-(5-hydroxymethyl-1,4-oxathian-2-yl)uracil, 1-(5-hydroxymethyl-1,4-oxathian-2-yl)uracil, 2-amino-6-chloro-9-(5-hydroxymethyl-1,4-oxathian-2-yl)purine, 9-(5-hydroxymethyl-1,4-oxathian-2-yl)guanine, 9-(5-hydroxymethyl-1,4-oxathian-2-yl)adenine and 2,6-diamino-9-(5-hydroxymethyl-1,4-oxathian-2-yl)purine.

8. A nucleoside derivative or a pharmaceutically acceptable salt thereof according to claim 5 selected from the group consisting of 1-(5-hydroxymethyltetiahydropyran-2-yl)cytosin, 5-fluoro-1-(5-hydroxymethyltetrahydropyran-2-yl)cytosine, 5-methyl-1-(5-hydroxymethltetrahydropyran-2-yl)cytosine, 1-(5-hydroxymethyltetrahydropyran-2-yl) thymine, 5-iodo-1-(5-hydroxymethyl-tetrahydropyran-2-yl) uracil, 5-bromo-1-(5-hydroxymethyltetrahydropyran-2-yl) uracil, 5-chloro-1-(5-hydroxymethyltetrahydropyran-2-yl) uracil, 5-fluoro-1-(5-hydroxymethyltetrahydropyran-2-yl) uracil, 1-(5-hydroxymethyltetrahydropyran-2-yl)uracil, 2-amino-6-chloro-9-(5-hydroxymethyltetrahydropyran-2-yl)purine, 9-(5-hydroxymethyltetrahydropyran-2-yl) guanine, 7-(5-hydroxymethyltetrahydropyran-2-)guanine, 9-(5-hydroxymethyltetrahydropyran-2-yl)adenine and 2,6-diamino-9-(5-hydroxymethyltetrahydropyran-2-yl) purine.

\* \* \* \* \*